United States Patent [19]

Braña et al.

[11] Patent Number: 5,703,089
[45] Date of Patent: Dec. 30, 1997

[54] DIHYDRODIBENZISOQUINOLINEDIONES

[75] Inventors: Miguel Fernandez Braña; José Maria Castellano Berlanga, both of Madrid, Spain; Cynthia Romerdahl, Wayland, Mass.

[73] Assignee: Knoll Aktiengesellschaft, Rheinland Pfalz, Germany

[21] Appl. No.: 699,205

[22] Filed: Aug. 19, 1996

Related U.S. Application Data

[63] Continuation of Ser. No. 332,382, Oct. 31, 1994, abandoned, which is a continuation-in-part of Ser. No. 233,998, Apr. 28, 1994, abandoned.

[51] Int. Cl.$^6$ ............................................. A61K 31/47
[52] U.S. Cl. .................................. 514/284; 546/76
[58] Field of Search ........................ 546/76; 514/284

[56] References Cited

U.S. PATENT DOCUMENTS

| | | | |
|---|---|---|---|
| 4,874,863 | 10/1989 | Braña | 546/100 |
| 4,874,883 | 10/1989 | Uphues et al. | 558/150 |
| 5,086,059 | 2/1992 | Ardeckey et al. | 546/76 |
| 5,416,089 | 5/1995 | Patten et al. | 514/284 |
| 5,554,622 | 9/1996 | Braña et al. | 514/284 |
| 5,616,589 | 4/1997 | Keilhauer et al. | 546/76 |

FOREIGN PATENT DOCUMENTS

| | | | |
|---|---|---|---|
| 92-00281 | 1/1992 | WIPO | 546/76 |
| 94-07862 | 4/1994 | WIPO | 546/76 |

OTHER PUBLICATIONS

Sami et al, Jour. Med Chem vol. 36 pp. 765–770, 1993.

Braña et al. AntiCancer Drug Design, vol. 8 pp. 257–268, 1993.

Miller et al BioOrg & Med. Chem. Lett. vol. 4 No. 13 pp. 1643–1648, 1994.

*Primary Examiner*—Donald G. Daus
*Attorney, Agent, or Firm*—Hamilton, Brook, Smith and Reynolds, P.C.

[57] ABSTRACT

Novel bis-1,2-dihydro-3H-dibenzisoquinoline-1,3-diones and their salts, processes for their preparation, pharmaceutical compositions containing them and methods of using them to treat malignancies, mainly human solid tumor carcinomas.

5 Claims, No Drawings

DIHYDRODIBENZISOQUINOLINEDIONES

This application is a continuation of application Ser. No. 08/332,382 filed Oct. 31, 1994, which is a Continuation-in-Part of 08/233,998 filed Apr. 28, 1994 both now abandoned.

DESCRIPTION

This invention relates to novel bis-1,2-dihydro-3H-dibenzisoquinoline-1,3-diones and their salts, processes for their preparation, pharmaceutical compositions containing them and methods of using them to treat malignancies, mainly human solid tumor carcinomas.

The use of bis-naphthalimides for the treatment of tumor carcinomas is already known (see e.g. U.S. Pat. Nos. 4,874,863, 5,086,059 and DE 4,232,739). Further, dibenzisoquinolines have been described (EP 536,208) which have anti-cancer activity.

The present invention relates to bis-1,2-dihydro-3H-dibenzisoquinoline-1,3-diones of the formula I

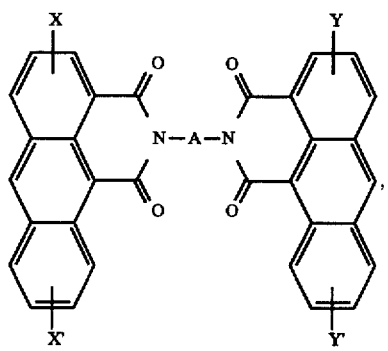

wherein X, X', Y, and Y' are identical or different and are each H, $NO_2$, $NH_2$, $C_1-C_6$-alkylamino, di-$C_1-C_6$ alkylamino, NH-$C_{1-6}$-acyl, OH, $C_1-H_6$-alkoxy, halogen, trihalomethyl, $C_1-C_6$-alkyl, formyl, $C_1-C_6$-alkylcarbonyl, ureyl, $C_1-C_6$-alkylureyl and A is a $C_4-C_{12}$-bridge which is interrupted at one, two or three points by a secondary or tertiary amino group, where two nitrogen atoms may additionally be bonded to one another by a $C_{1-4}$-alkylene group, and the salts thereof with physiologically tolerated acids.

One class of compounds of the present invention is bis-1,2-dihydro-3H-dibenzisoquinoline-1,3-diones of the formula I in which at least one of X, X', Y, and Y' are not H, i.e., wherein X, X', Y, and Y' are identical or different and are selected from the group consisting of $NO_2$, $NH_2$, NH-lower acyl, $C_{1-6}$-alkylamino, di-$C_{1-6}$-alkylamino, OH, $C_{1-6}$-alkoxy, halogen, trihalomethyl, $C_{1-6}$-alkyl, formyl, $C_{1-6}$-alkylcarbonyl, ureyl, and $C_{1-6}$-alkylureyl. It is currently preferred in various embodiments of this class for none of X, X', Y, and Y' to be $NO_2$.

One subclass of the foregoing is bis-1,2-dihydro-3H-dibenzoisoquinoline-1,3-diones of the formula I wherein at least one of X, X', Y and Y' is $NH_2$, NH-lower acyl, $C_{1-6}$-alkylamino or di-$C_{1-6}$-alkylamino. This class includes, among others, compounds of the formula I in which X and Y are H; X' and Y' are $NHCOCH_3$; and —A— is —CH($CH_3$)—$CH_2$—NH—$CH_2$—$CH_2$—NH—$CH_2$—CH($CH_3$)— or —$(CH_2)_2$—NH—$(CH_2)_3$—NH—$(CH_2)_2$—.

Another class of compounds of the present invention is bis-1,2-dihydro-3H-dibenzisoquinoline-1,3-diones of the formula I in which A is

or

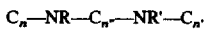

wherein $C_n$, $C_{n'}$, and $C_{n''}$ are identical or different and are each $C_{1-4}$-alkylene radicals and R and R' are H, $C_{1-4}$-alkyl, benzyl, phenyl, or phenyl substituted by a halogen atom or a $C_{1-4}$-alkyl group or an amino group.

One subclass of such compounds is bis-1,2-dihydro-3H-dibenzoisoquinoline-1,3-diones of the formula I wherein the bridging moiety A joining the two ring systems is:

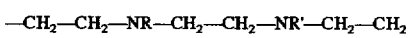

or

wherein R and R' are as previously defined. These compounds include those in which X and X' and R and R' are all H.

Compounds I of the present invention can be synthesized according to the following methods:

1. by reacting an anthracene-1,9-dicarboxylic anhydride of the formula II with a polyamine of the formula III:

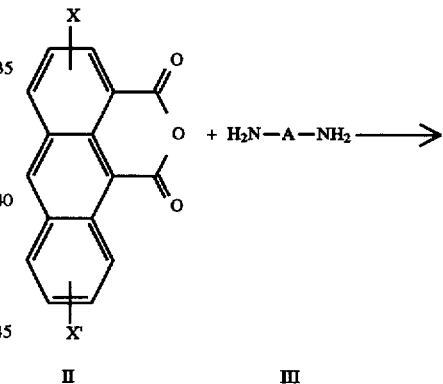

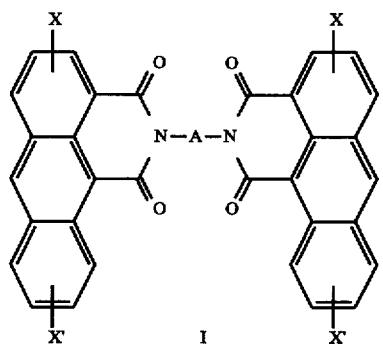

Instead of the acid anhydride the corresponding dicarboxylic acid dialkyl ester or dicarboxylic acid halide may be used;

2. by reacting an anthracene-1,9-dicarboxylic imide VI with a compound of the formula VII:

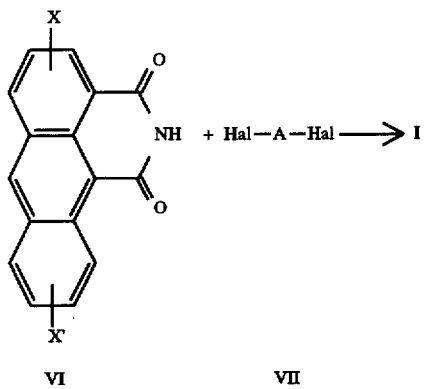

wherein Hal means a halogen atom, preferably bromine;

3. if A is interrupted by two nitrogen atoms—by reacting a compound of the formula IV with a diamine of the formula V:

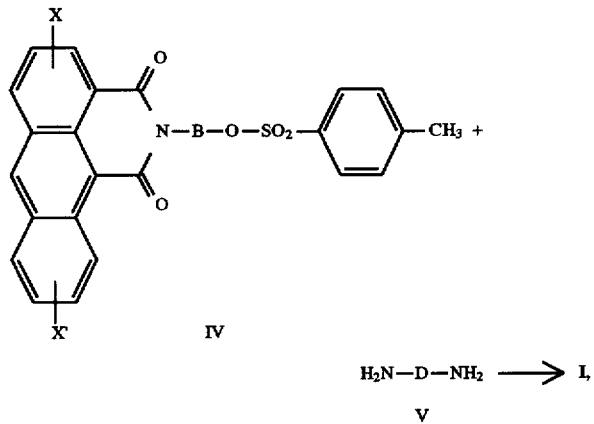

wherein B plus D are alkylene residues so that 2 B plus D contain 4 to 12 carbon atoms.

Reaction 1 is performed by reacting the compound II with a half equivalent of a polyamine of the formula III in an organic solvent such as alcohols (especially ethanol), acetone, DMSO, THF, DMF, dioxane, aromatic hydrocarbons (especially toluene), or any inert solvent. The temperature of the reaction should be between −20° C. and the boiling temperature of the solvent. Fairly high temperatures are preferred.

Reactions 2 and 3 are performed under the same conditions, but in the presence of a base.

The final product is filtered off or the reaction mixture is evaporated to dryness under reduced pressure and the residue is purified in conventional manner by crystallization or chromatography.

The starting compounds II-VI can be prepared by methods known from the literature, or they are commercial products.

Compounds I can also be synthesized according to the following method:

Reacting a compound of formula II or the corresponding dialkylester or acid halide with a polyamine of the formula III to a compound of formula VIII

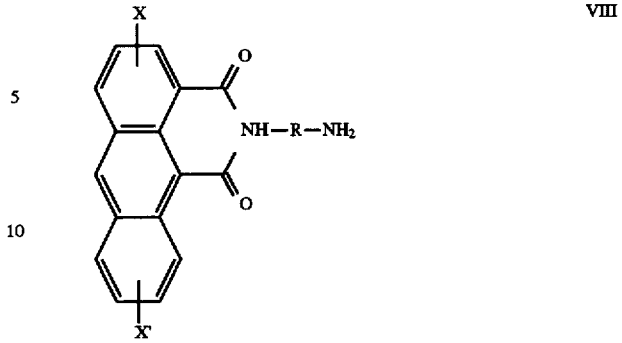

which is reacted with a compound of the formula II.

The bis-1,2-dihydro-3H-dibenzoisoquinoline-1,3-diones so obtained are used per se, or they can be acidified with the appropriate mineral or organic acid to produce a pharmaceutically acceptable salt, e.g. the methanesulfonate or the acetate salt, which can be recovered by filtration. Salts of the free base can also be prepared by acidifying a suspension of the free base in ethyl alcohol, dichloromethane, ether, etc. with the appropriate mineral or organic acid and collecting by filtration the solid thus formed. Other acids for salt formation are known from the art, see e.g., Braña et al., U.S. Pat. No. 4,874,863.

The present invention further encompasses pharmaceutical compositions containing a tumor-inhibiting compound according to the invention together with a pharmaceutically acceptable carrier. It also relates to methods for treating tumors in mammals comprising administration of a tumor-inhibiting amount of a compound according to the invention to a mammal with such a tumor. The compounds according to the invention may be formulated into pharmaceutical compositions and administered to patients using conventional materials and methods such as are described in Braña et al., U.S. Pat. Nos. 4,874,863 and 5,206,249 (the contents of both of which are hereby incorporated herein by reference). See especially U.S. Pat. No. 5,206,249 at column 22, line 10 through the end of column 23.

The compounds according to the invention have cytotoxic activity useful in the treatment of various cancers. These compounds can be evaluated for relative efficacy in in vitro and in vivo models such as are generally accepted in this art, including those described in U.S. Pat. No. 5,206,249 (see especially column 19 to column22, line 9). Efficacy in such models is indicative of utility in the treatment of solid tumors in human patients and evidences important therapeutic utility in the treatment of cancer, particularly solid tumor carcinomas, such as colon carcinoma, breast tumors, prostate cancer, and non-small lung carcinoma. The new compounds exhibit better properties than prior art compounds with regard to activity, toxicity and/or solubility.

A. In vitro methodology

Cytotoxicity may be measured using standard methodology for adherent cell lines such as the microculture tetrazolium assay (MTT). Details of this assay have been published Cancer Research 48:589–601, 1988). Exponentially growing cultures of tumor cells such as the HT-29 colon carcinoma or LX-1 lung tumor are used to make microtiter plate cultures. Cells are seeded at 5000–20,000 cells per well in 96-well plates (in 150 μl of media), and grown overnight at 37° C. Test compounds are added, in dilutions varying from $10^{-4}$M to $10^{-10}$M. The cells are then incubated for 48–72 hours. To determine the number of viable cells in each well, the MTT dye is added (50 μl of 3 mg/ml solution of 3-(4,5-dimethylthiazol-2-yl)-2,5-diphenyltetrazolium bromide in saline). This mixture is incubated at 37° C. for 5 hours, and then 50 μl of 25% strength SDS (pH 2) is added to each well. After overnight incubation, the absorbance of each well at 550 nm is read using an ELISA reader. The values for the mean +/− SD of data from quadruplicate wells are calculated, using the formula % T/C (% cells treated/control).

$$\frac{OD \text{ of trated cells}}{OD \text{ of control cells}} \times 100 = \% \, T/C$$

The concentration of test compound which gives a T/C of 50% growth inhibition is designated as the $IC_{50}$.

B. In vivo methodology

Compounds according to the invention may be further tested in any of the various preclinical assays for in vivo activity which are indicative of clinical utility. Such assays may be conducted with human tumors implanted in nude mice as xenografts or mouse tumors implanted in conventional mice in the strain of origin (syngeneic), as is well known in this field. Test compounds are evaluated for their antitumor efficacy following administration to the tumor-bearing mice.

More specifically, human tumors which have been grown in athymic nude mice or mouse tumors grown in their synergeneic host are transplanted into new recipient animals, using either tumor fragments which are about 50 mg in size or 1×10⁶ cells harvested from ascites fluid. The day of transplantation is designated as day 0 and the host mice are subsequently injected intravenously or intraperitoneally with the test compounds, in group of 5 to 10 mice per dose level. The compounds are administered either as a single dose or on an intermittent or frequent dosing schedule at doses from 0.1 to 100 mg/kg body weight. Tumor size of solid tumors are measured by vernier calipers in two directions and the volume estimated by the formula:

(length×width$^2$)/2=mm$^3$ (tumor volume).

Mean tumor volumes are calculated for each treatment group, and treated/control (T/C) values determined for each group relative to the untreated control tumors. The data may be evaluated as follows. A T/C value of 1.0 or greater indicates that the compound had no effect on tumor growth, while values <1.0 indicate some reduction in tumor mass. Values of 0.15–0.49 may be considered to reflect moderate activity, <0.01–0.14 good to excellent activity. Outstanding activity indicates a compound which provides complete regression of tumor material (no visible tumor mass following therapy). Compounds yielding T/C values >0.50 are considered inactive.

Life span studies following i.p. administration of tumor cells are evaluated on the base of median survival time (MST). The MST of drug treated (T) mice are compared to the MST of control (C) mice and expressed as T/C percent. Compounds producing a T/C percent of >100% indicates some reduction in tumor burden. Values of 125 to 150% may be considered to reflect moderate activity, values of 150 to 200% good to excellent activity, and >200% outstanding activity.

Inhibition of HT-29 tumor cell proliferation[a].

| Example | IC 50 |
|---|---|
| 1 | $4 \times 10^{-9} M^b$ |
| | $5 \times 10^{-9} M$ |
| 1 $_2CH_3—SO_3H$ salt | $1 \times 10^{-8} M^c$ |
| | $2 \times 10^{-8} M$ |
| 2 | $1 \times 10^{-8} M^b$ |
| | $8 \times 10^{-9} M$ |
| 3 | $2 \times 10^{-7} M^b$ |
| | $2 - 10^{-7} M$ |
| 4 | $9 \times 10^{-8} M^d$ |
| | $5 \times 10^{-8} M$ |
| 5 | $2 \times 10^{-9} M^b$ |
| | $8 \times 10^{-8} M$ |
| 6 | $8 \times 10^{-9} M^b$ |
| | $3 \times 10^{-8} M$ |
| 7 | $2 \times 10^{-8} M^b$ |
| | $2 \times 10^{-8} M$ |
| 8 | $>1 \times 10^{-7} M^d$ |
| | $2 \times 10^{-6} M$ |
| 9 | $2 \times 10^{-8} M^d$ |
| | $2 \times 10^{-8} M$ |
| 10 | $1 \times 10^{-7} M^b$ |
| | $9 \times 10^{-8} M$ |
| 11 | $1 \times 10^{-7} M^b$ |
| | $8 \times 10^{-8} M$ |
| 12 | $3 \times 10^{-8} M^e$ |
| | $4 \times 10^{-8} M$ |
| 13 | $1 \times 10^{-7} M^e$ |
| | $9 \times 10^{-8} M$ |
| 14 | $7 \times 10^{-8} M^c$ |
| | $8 \times 10^{-8} M$ |
| 15 | $8 \times 10^{-9} M^c$ |
| | $1 \times 10^{-8} M$ |
| 16 | $9 \times 10^{-10} M^b$ |
| | $2 \times 10^{-9} M$ |

[a]Dihydrodibenzoquinolinedione cytotoxicity studies were performed as follows: HT-29 cells were seeded (5000) into each well of 96 well dishes. After plating overnight a titration of dihydrodibenzoquinolinedione was added giving a final volume of 200 ul. Following incubation for 72 h 50 ul of MTT (3 mg/ml) in PBS was added to each well and incubated for 5 hours at 37° C. The reaction was stopped by the addition of 50 ul of 25% SDS, pH 2. After an overnight incubation at 37° C. the absorbance, due to metabolized MTT, was read with a plate reader at 550 nm. Cytotoxicity was calculate as the well absorbance expressed as a percentage on non-drug treated control. All estimates were made in duplicate.
[b]10⁻²M stock solution made in 10% acetic acid then diluted in media.
[c]10⁻²M stock solution made in 10% DMSO then diluted in media.
[d]10⁻⁴M stock solution made in 10% acetic acid/10% DMSO then diluted in media.
[e]10⁻²M stock suspention made in DMSO then diluted in media to form a solution.

In vivo anti-tumor activity of a Dihydrodibenzoquinolinedione analog on M5076 murine sarcoma[a].

| Dose (mg/kg) | MST | % T/C |
|---|---|---|
| Experiment 1 | | |
| Control | 19.5 | |
| 4 | toxic | toxic |
| 2.6 | 24 | 123 |
| 1.8 | 30 | 154 |
| Experiment 2 | | |
| Control | 23.5 | |
| 2.7 | toxic | toxic |

-continued

| Dose (mg/kg) | MST | % T/C |
|---|---|---|
| 1.8 | 23 | 98 |
| 1.2 | 30 | 128 |

*C57BL/6 mice (6 per group) were inoculated with $10^6$ M5076 cells on day 0. Mice were treated on days 1,5 and 9 with the dimethanesulfonate salt of example 1 at the dose levels shown. Mice died as a consequence of tumor burden with median survival times (MST) as shown. In both studies meaningful antitumor activity was produce as indicated by a treated MST/Control MST percentage (% T/C) being reproducibly greater than 125%.

The invention can be further understood by referring to the following examples, in which parts and percentages are by weight unless otherwise specified.

EXAMPLE 1

N,N'-Bis[2-(1,2-dihydro-1,3-dioxo-3H-dibenz[de,h]isoquinoline-2-yl)ethyl]-1,3-propanediamine A mixture of 1.6 g (6 mmol) of anthracene-1,9-dicarboxylic anhydride in 40 ml of toluene was treated with 0.5 g (3 mmol) of N,N'-bis(2-aminoethyl)-1,3-propanediamine dissolved in 10 ml of toluene. The mixture was refluxed for 4 h and then filtered. The solution was allowed to cool and the solid formed was filtered, washed, dried and recrystallized from toluene. 0.93 g (50%) of N,N'-bis[2-(1,2-dihydro-1,3-dioxo-3H-dibenz[de,h]isoquinolin-2-yl)ethyl]-1,3-propanediamine were obtained. M.p. 191° C. (toluene). $^1$H-NMR (CDCl$_3$) δ=1.84 (q, 2H, J=6 Hz, —CH$_2$—); 2.74 (broad, s, 2H, NH); 2.89 (t, 4H, J=6 Hz, CH$_2$); 3.02 (t, 4H, J=6 Hz, CH$_2$); 4.31 (t,4H, J=6 Hz, CH$_2$); 7.54 (m, 4H, H-5 and H-9); 7.73 (m, 2H,H-10); 7.89 (d, 2H, J=8 Hz, H-8); 8.22 (d, 1H, J=8 Hz, H-4); 8.51 (s,2H, H-7); 8.57 (d, 2H, J=8 Hz, H-6); 9.78 (d,2H, J=8 Hz, H-11) p.p.m.. Anal. Calculated for $C_{39}H_{32}N_4O_4$: C 75.46; H 5.19; N 9.02. Found: C 75.14; H 5.37; N 8.78. Acetate m.p. 155° C. Methanesulfonate m.p. 243° C.

EXAMPLE 2

N,N'-Bis[2-(1,2-dihydro-1,3-dioxo-3H-dibenz[de,h]isoquinolin-2-yl)ethyl]-1,2-ethylenediamine.
As example 1. Yield 66%. M.p. 203° C. (DMF-H$_2$O)

EXAMPLE 3

N,N'-Bis[3-(1,2-dihydro-1,3-dioxo-3H-dibenz[de,h]isoquinolin-2-yl)propyl]-1,4-butanediamine.
As example 1. Yield 46%. M.p. 183° C. (toluene).

EXAMPLE 4

[3-(1,2-dihydro-1,3-dioxo-3H-dibenz[de,h]isoquinolin-2-yl)propyl][4-(1,2-dihydro-1,3-dioxo-3,4-dibenz[de,h]isoquinolin-2-yl)butyl]amine.
As example 1. Yield 41%. M.p. 244° C. (DMF).

EXAMPLE 5

N,N'-Bis[2-1,2-dihydro-1,3-dioxo-3H-dibenz[de,h]isoquinolin-2-yl)ethyl]-1,4-butanediamine.
As example 1. Yield 40%. M.p. 179° C. (toluene).

EXAMPLE 6

Bis[3-(1,2-dihydro-1,3-dioxo-3H-dibenz[de,h]isoquinolin-2-yl)propyl]methylamine.
As example 1. Yield 35%. M.p. 194° C. (toluene).

EXAMPLE 7

Bis[3-(1,2-dihydro-1,3-dioxo-3H-dibenz[de,h]isoquinolin-2-yl)propyl]amine.
As example 1. Yield 83%. M.p. 184° C. (toluene).

EXAMPLE 8

[2-(1,2-Dihydro-1,3-dioxo-3H-dibenz[de,h]isoquinolin-2-yl)ethyl][3-(1,2-dihydro-1,3-dioxo-3H-dibenz[de,h]isoquinolin-2-yl)propyl]amine.
As example 1. Yield 78%. M.p. 260° C. (DMF).

EXAMPLE 9

Bis[2-(1,2-dihydro-1,3-dioxo-3H-dibenz[de,h]isoquinolin-2-yl)ethyl]amine.
As example 1. Yield 53%. M.p. 271° C. (DMF-H$_2$O).

EXAMPLE 10

N,N'-Bis[3-(1,2-dihydro-1,3-dioxo-3H-dibenz[de,h]isoquinolin-2-yl)propyl]-1,2-ethylenediamine.
As example 1. Yield 61%. M.p. 180° C. (toluene).

EXAMPLE 11

N,N'-Bis[3-(1,2-dihydro-1,3-dioxo-3H-dibenz[de,h]isoquinolin-2-yl)propyl]-1,3-propanediamine.
As example 1. Yield 41%. M.p. 140° C. (toluene).

EXAMPLE 12

N,N'-Bis[2-(1,2-dihydro-8-nitro-1,3-dioxo-3H-dibenz[de,h]isoquinolin-2-yl)ethyl]-1,3-propanediamine.
As example 1. Yield 52%. M.p. >340° C. (toluene)

EXAMPLE 13

N,N'-Bis-[2-(1,2-dihydro-8-nitro-1,3-dioxo-3H-dibenz[de,h]isoquinolin-2-yl)ethyl]1,3-ethylenediamine.
As example 1. Yield 57%. M.p. >340° C. (toluene)

EXAMPLE 14

N,N'-Bis[2-(1,2-dihydro-1,3-dioxo-3H-dibenz[de,h]isoquinolin-2-yl)ethyl]-N,N'-dimethyl-1,2-ethylenediamine.
As example 1. Yield 77%. M.p. 255° C. (toluene).

EXAMPLE 15

N,N'-Bis[2-(1,2-dihydro-1,3-dioxo-3H-dibenz[de,h]isoquinolin-2-yl)ethyl]-1,5-pentanediamine.
As example 1. Yield 25%. M.p. 122° C. (toluene).

EXAMPLE 16

N,N'-Bis[2-(1,2-dihydro-1,3-dioxo-3H-dibenz[de,h]isoquinolin-2-yl)ethyl]hexahydropyrimidine.

A mixture of 0.5 g (0.8 mmol) of N,N'-Bis[2-(1,2-dihydro-1,3-dioxo-3H-dibenz[de,h]isoquinolin-2-yl)ethyl]-1,3-propanediamine and 1 ml of 36% formaldehyde in 100 ml of ethanol was refluxed for 7 hours. The solid was filtered, washed, dried, and recrystallized from toluene. 0.3 g (58%) of N,N'-bis[2-(1,2-dihydro-1,3-dioxo-3H-dibenz[de,h]isoquinolin-2-yl)ethyl]hexahydropyrimidine were obtained. M.p. 222° C. (toluene).

EXAMPLE 17

N,N'-Bis[2-(1,2-dihydro-1,3-dioxo-3H-dibenz[de,h]isoquinolin-2-yl)ethyl]-1,3-propanediamine A mixture of 1.47 g (5 mmol) of anthracene-1,9-dicarboxylic acid dimethyl ester in 50 ml of toluene is treated with 0.4 g (2.5 mmol) of N,N'-bis(2-aminoethyl)-1,3-propanediamine in 20 ml of toluene. The suspension is refluxed for 24 hours and then cooled to room temperature. The solid is filtered, dried, and crystallized from toluene to give 0.65 g (42%) of N,N'-bis[2-(1,2-dihydro-1,3-dioxo-3H-dibenz[de,h]-isoquinolin-2-yl)ethyl]-1,3-propanediamine. M.p. 191° C.

EXAMPLE 18

N,N'-Bis[2-(1,2-dihydro-1,3-dioxo-3H-dibenz[de,h]isoquinolin-2-yl)ethyl]-1,3-propanediamine 0.4 g (2.5 mmol) of N,N'-bis 2-aminoethyl)-1,3-propanediamine in 20 ml of toluene are added to a mixture of 1.51 g (5 mmol) of anthracene-1,9-dicarboxylic acid dichloride in 50 ml of toluene. The suspension is refluxed for 20 hours and then cooled to room temperature. The solid is filtered, dried and crystallized from toluene to give 0.54 g (35%) of N,N'-bis[2-(1,2-dihydro-1,3-dioxo-3H-di-benz[de,h]isoquinolin-2-yl)ethyl]-1,3-propanediamine. M.p. 191° C.

EXAMPLE 19

N,N'-Bis[2-(1,2-dihydro-1,3-dioxo-3H-dibenz[de,h]isoquinolin-2-yl)ethyl]-1,3-propanediamine A. 2-(2-Hydroxyethyl)-1,2-dihydro-3H-dibenz[de,h]isoquinoline-1,3-dione A mixture of 1.51 g (6 mmol) of anthracene-1,9-dicarboxylic acid anhydride and 0.4 g (6.5 mmol) of ethanolamine in 50 ml of toluene is refluxed for 5 hours and then cooled to room temperature. The solid is filtered, dried and crystallized from toluene to give 1.5 g (85%) of 2-(2-hydroxyethyl)-1,2-dihydro-3H-dibenz[de,h]isoquinoline-1,3-dione. M.p. 211° C.

B. 2-[2-(p-Toluenesulfonyloxy)ethyl]-1,2-dihydro-3H-dibenz[de,h]isoquinoline-1,3-dione A mixture of 1.01 g (3.5 mmol) of 2-(2-hydroxyethyl)-1,2-dihydro-3H-dibenz[de,h]isoquinoline-1,3-dione in 10 ml of pyridine is treated with 0.69 g (3.6 mmol) of p-toluenesulfonyl chloride. The mixture is stirred at room temperature for 24 hours and poured into 50 ml of cold water. The solid is collected, washed with water, dried in vacuo, and crystallized from dimethylformamide water to give 1.2 g (77%) of 2-[2-(p-toluenesulfonyloxy)ethyl]-1,2-dihydro-3H-dibenz-[de,h]isoquinoline-1,3-dione. M.p. 240° C.

C. N,N'-Bis[2-(1,2-dihydro-1,3-dioxo-3H-dibenz[de,h]isoquinolin-2-yl)ethyl]-1,3-propanediamine A mixture of 2.2 g (5 mmol) of 2-[2-(p-toluenesulfonyloxy)ethyl]-1,2-dihydro-3H-dibenz[de,h]isoquinoline-1,3-dione, 0.4 g (2.5 mmol) of 1,3-propanediamine in 200 ml of acetonitrile is refluxed in the presence of 0.6 g (5.6 mmol) of sodium carbonate for 24 hours. The reaction mixture is concentrated in vacuo. The residue is treated with water (100 ml) and extracted with dichloromethane. The organic layers are combined, dried with magnesium sulfate, filtered, and concentrated in vacuo. The residue is chromatographed, eluting with dichloromethane, methanol, acetic acid (80:15:5). The appropriate fractions are combined, concentrated in vacuo and crystallized from toluene to give 0.3 g (20%) of N,N'-bis[2-(1,2-dihydro-1,3-dioxo-3H-dibenz[de,h]isoquinolin-2-yl)ethyl]-1,3-propanediamine. M.p. 191° C.

EXAMPLE 20

N,N'-Bis[2-(1,2-dihydro-1,3-dioxo-3H-dibenz[de,h]isoquinolin-2-yl)ethyl]-1,3-propanediamine A. 1,2-Dihydro-3H-dibenz[de,h]isoquinoline-1,3-dione 1.51 g (6 mmol) of anthracene-1,9-dicarboxylic acid anhydride was treated with 10 ml of ammonium hydroxide (28%). After refluxing for 16 hours the solid was collected, washed with water, dried in vacuo, and crystallized from dimethylformamide-water to give 1.3 g (86%) of 1,2-dihydro-3H-dibenz[de,h]isoquinoline-1,3-dione. M.p. 310° C.

B. N,N'-Bis[2-(1,2-dihydro-1,3-dioxo-3H-dibenz[de,h]isoquinolin-2-yl)ethyl]-1,3-propanediamine A mixture of 1.23 g (5 mmol) of 1,2-dihydro-3H-dibenz[de,h]isoquinoline-1,3-dione in 100 ml of ethanol is treated with 280 mg (5 mmol) of potassium hydroxide in 50 ml of ethanol. After refluxing for 3 hours, 0.65 g (2.5 mmol) of N,N'-bis(2-bromoethyl)-1,3-propanediamine in 50 ml of ethanol are added and the whole is refluxed for 24 hours. The reaction mixture is concentrated in vacuo. The residue is treated with water (100 ml) and extracted with dichloromethane. The organic layers are combined, dried with magnesium sulfate, filtered, and concentrated in vacuo. The residue is chromatographed, eluting with dichloromethane, methanol, acetic acid (80:15:5). The appropriate fractions are combined, concentrated in vacuo and crystallized from toluene to give 0.31 g (20%) of N,N'-bis[2-(1,2-dihydro-1,3-dioxo-3H-dibenz[de,h]isoquinolin-2-yl)ethyl]-1,3-propanediamine. M.p. 191° C.

EXAMPLE 21

N,N'-Bis[2-(1,2-dihydro-1,3-dioxo-3H-dibenz[de,h]isoquinolin-2-yl)ethyl]-1,3-propanediamine A. N-[2-(1,2-Dihydro-1,3-dioxo-3H-dibenz[de,h]isoquinolin-2-yl)ethyl]-N'-(2-aminoethyl)-1,3-propanediamine A solution of 5.0 g (31 mmol) of N,N'-bis(2-aminoethyl)-1,3-propanediamine in 200 ml of ethanol 99% is treated with 1.5 g (6 mmol) of anthracene-1,9-dicarboxylic acid anhydride in 100 ml of ethanol and stirred for 24 hours at room temperature. The solid is collected on a filter, washed with ethanol and crystallized from ethanol to give 0.5 g (20%) of N-[2-(1,2-dihydro-1,3-dioxo-3H-dibenz[de,h]isoquinolin-2-yl)ethyl]-N'-(2-aminoethyl)-1,3-propanediamine. M.p. 150° C.

B. N,N'-Bis[2-(1,2-dihydro-1,3-dioxo-3H-dibenz[de,h]isoquinolin-2-yl)ethyl]-1,3-propanediamine A mixture of 1.0 g (2.5 mmol) of N-[2-(1,2-dihydro-1,3-dioxo-3H-dibenz[de,h]isoquinolin-2-yl)ethyl]-N'-(2-aminoethyl)-1,3-propanediamine in 50 ml of toluene was treated with 0.62 g (2.5 mmol) of anthracene-1,9-dicarboxylic acid anhyride in 10 ml of toluene, refluxed for 6 hours, and cooled to room temperature. The solid was collected, dried in vacuo, and crystallized from toluene to give 0.8 g 48% of N,N'-Bis[2-(1,2-dihydro-1,3-dioxo-3H-dibenz[de,h]isoquinolin-2-yl)ethyl]-1,3-propanediamine. M.p. 191° C.

We claim:
1. A compound of the formula,

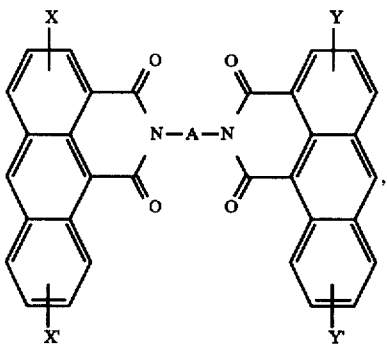

wherein X, X', Y and Y' are identical or different and are each H, $NO_2$, $NH_2$, $C_1$–$C_6$-alkylamino, di-$C_1$–$C_6$-alkylamino, NH— $C_1$–$C_6$-acyl, OH, $C_1$–$C_6$-alkoxy, halogen, trihalomethyl, $C_1$–$C_6$-alkyl, formyl, $C_1$–$C_6$-alkylcarbonyl, ureyl, $C_1$–$C_6$-alkylureyl, and A is a $C_4$–$C_{12}$-bridge which is interrupted at one, two or three points by a secondary or tertiary amino group, where two nitrogen atoms separated by 4 or fewer carbon atoms may additionally be bonded to one another by a $C_{1-2}$-alkylene group, or a salt thereof with a physiologically tolerated acid.

2. A bis-1,2-dihydro-3H-dibenzisoquinoline-1,3-dione as claimed in claim 1 where X, X', Y and Y' are hydrogen.

3. A bis-1,2-dihydro-3H-dibenzisoquinoline-1,3-dione as claimed in claim 1 as a salt of acetic or methanesulfonic acid.

4. A pharmaceutical composition for treating solid tumors comprising a pharmaceutically acceptable carrier and a therapeutically effective amount of a compound as claimed in claim 1.

5. A method of treating a colon tumor in a human comprising administering to the human with such tumor a tumor-inhibiting amount of a compound as claimed in claim 1.

* * * * *